United States Patent [19]
Hamano et al.

[11] Patent Number: 5,415,287
[45] Date of Patent: May 16, 1995

[54] ENDOSCOPE HOLDING AND STORING APPARATUS

[75] Inventors: Masahiko Hamano, Hino; Toshiaki Nishikori, Sagamihara; Tsuguhisa Sasai, Tsukui; Mutsumi Oshima, Machida; Hiroyuki Ushifusa; Hideyuki Shouji, both of Hachioji; Atsushi Amano, Tama; Kouji Okada, Yokohama; Kenya Inomata, Mitaka; Kazufumi Takamizawa, Choufu, all of Japan

[73] Assignee: Olympus Optical Co., Ltd., Tokyo, Japan

[21] Appl. No.: 340,482

[22] Filed: Nov. 14, 1994

Related U.S. Application Data

[63] Continuation of Ser. No. 84,919, Jul. 1, 1993, abandoned, which is a continuation-in-part of Ser. No. 51,812, Apr. 26, 1993, abandoned, which is a continuation of Ser. No. 820,994, Jan. 15, 1992, abandoned.

[30] Foreign Application Priority Data

Jul. 3, 1992 [JP] Japan .................................. 4-177191

[51] Int. Cl.⁶ .............................................. B65D 83/10
[52] U.S. Cl. .................................... 206/363; 206/364; 383/33; 128/DIG. 26; 604/317; 604/322
[58] Field of Search ................ 206/363, 364, 438; 383/33; 128/DIG. 26; 604/317, 322, 174, 54, 263, 280

[56] References Cited

U.S. PATENT DOCUMENTS

| | | | |
|---|---|---|---|
| 4,025,015 | 5/1977 | Kolic | 128/DIG. 26 |
| 4,053,280 | 10/1977 | Salisbury . | |
| 4,312,447 | 1/1982 | McWilliams | 206/438 |
| 4,478,332 | 10/1984 | Wiestmiller | 206/363 |
| 4,711,352 | 12/1987 | Williams et al. | 206/363 |
| 4,747,701 | 5/1988 | Perkins | 383/33 |
| 4,773,768 | 9/1988 | Leeper | 604/322 |
| 4,997,084 | 3/1991 | Opie et al. | 206/364 |
| 5,031,775 | 7/1991 | Kane | 206/438 |
| 5,148,940 | 9/1992 | Mendise | 604/317 |

FOREIGN PATENT DOCUMENTS 2-58403 4/1990 Japan .

*Primary Examiner*—Bryon P. Gehman
*Assistant Examiner*—Marie Denise Patterson
*Attorney, Agent, or Firm*—Armstrong, Westerman, Hattori, McLeland & Naughton

[57] ABSTRACT

A holding apparatus for holding at least an operational part of an endoscope is provided as a removable unit of an endoscope system storage rack. An endoscope storage case in which an insertion tube of an endoscope hung on the holding apparatus is removably provided in the storage rack below the holding apparatus. The endoscope storage case stores at least a used endoscope.

10 Claims, 17 Drawing Sheets

ENDOSCOPE HOLDING AND STORING APPARATUS

This application is a continuation of application Ser. No. 08/084,919 filed Jul. 1, 1993, now abandoned, which is a continuation-in-part application of application Ser. No. 08/051,812, filed Apr. 26, 1993, now abandoned, which is a continuation of application Ser. No. 07/820,994, filed Jan. 15, 1992, now abandoned.

BACKGROUND OF THE INVENTION

1. Field of the Invention

The present invention relates to an endoscope holding and storing apparatus which catches and holds an endoscope on an endoscope system storage rack or a system cart and which makes transportation of an used endoscope easier.

2. Related Art Statement

In recent years, endoscopes have been widely used in the field of medical treatment. When an elongated insertion tube of an endoscope is inserted into the body cavity, the endoscope can perform various medical treatments, such as picking tissues in the body cavity and an operation using treatment tools inserted into a treatment tool channel to satisfy a demand.

An endoscope is relatively long and has an insertion tube. In addition, the insertion tube is inserted into the body cavity and should be kept clean before the endoscope is used. Therefore, an apparatus which holds the endoscope before an operation is proposed, for example, in Japanese Utility Model Application Laid Open No. 58403/1990. This endoscope holding and storing apparatus is provided with a rack 304 on the upper part of a rod member 302 fixed on a light source apparatus or on a side of a system cart 303 as shown in FIG. 1. Two concave holding parts 301 are arranged on The rack 304. The endoscope holding and storing apparatus holds the two concave holding parts approximately horizontal state. However, in the aforesaid endoscope holding and storing apparatus, it is possible that an unused and clean endoscope which was washed and disinfected, as well as a used endoscope which was not clean are caught and held by the same holding and storing apparatus. Further, the aforesaid endoscope holding and storing apparatus does not consider the transportation of a used endoscope.

FIG. 2 shows the construction in which an endoscope is caught by a hook provided in a system cart through a holder 312 fitted to a proximal operation part 311 of an endoscope. However, in spite of this construction it is possible that not only an unused and clean endoscope but also a used and unclean endoscope can be held by the hook provided in the system cart.

SUMMARY OF THE INVENTION

An object of the present invention is to provide an endoscope holding and storing apparatus in which an unused and clean endoscope that was washed and disinfected can be held and a used endoscope is stored as it is in a storage case that is replaced with a position into which an insertion tube is inserted when a used endoscope is hung on an endoscope holder can be transported to a place to be washed and disinfected.

Another object of the present invention is to provide an endoscope holding and storing apparatus in which an endoscope holder holds only an unused and clean endoscope which was washed and disinfected.

Further, another object of the present invention is to provide an endoscope holding and storing apparatus in which an endoscope holder holds a clean endoscope and a used endoscope, and is stored in a storage case with the used endoscope after the used endoscope is hung, and transported to a place to be washed and disinfected.

Further, another object of the present invention is to provide an endoscope holding and storing apparatus in which a used endoscope that is hung on a removed endoscope holder is stored in a storage case and can be transported.

The endoscope holding and storing apparatus of this invention comprises an endoscope holder catching and holding at least an operation part of an endoscope or its adjacent part, and a storage case in a storable position of at least an insertion tube of the endoscope when the endoscope is hung on the endoscope holder.

The other characteristics and advantages of the present invention will be sufficiently apparent from the following explanation.

BRIEF DESCRIPTION OF THE DRAWINGS

FIG. 3 is a perspective view showing a construction of an endoscope system;

FIG. 4 is a perspective view showing an example in which an endoscope system is used;

FIG. 5 is a perspective view showing an endoscope and endoscope holder in an endoscope system storage rack;

FIG. 6 is a perspective view showing a proximal operation part of an endoscope;

FIG. 7 is a perspective view showing an endoscope holder and an endoscope holder attaching part provided on a side of an endoscope system storage rack to which the endoscope holder is attached;

FIG. 8 is a perspective view showing a storage case attached to an endoscope system storage rack;

FIG. 9 is a perspective view of a storage case;

FIG. 10 is a perspective view showing a disposable bag attached to an inside of a storage case;

FIG. 11 is a perspective view showing a fitting tape provided on a disposable bag;

FIG. 12 is a perspective view of a storage case;

FIG. 13 is a perspective view of a storage case showing a state from which a cup holding part is removed;

FIG. 14 is a perspective view of a storage case showing a state in which an endoscope is held and stored;

FIG. 15 is an outline of the sectional view of FIG. 14;

FIG. 16 is an explanatory diagram showing a state in which a disposable bag is fitted to a storage case;

FIG. 17 is a perspective view showing a transformed example of a storage case;

FIG. 22 is a perspective view of an endoscope system storage rack;

FIG. 23 is an explanatory diagram of a storage case;

FIG. 24 is a perspective view showing an endoscope system storage rack;

FIG. 25 is an explanatory diagram of a storage case;

DETAILED DESCRIPTION OF THE PREFERRED EMBODIMENTS

Figure 1:
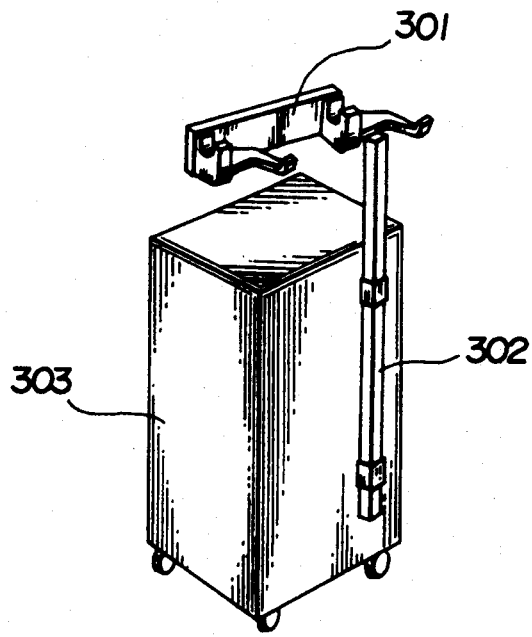
FIG. 1 is a perspective of an endoscope holding and storing apparatus of the prior art.
Figure 2:
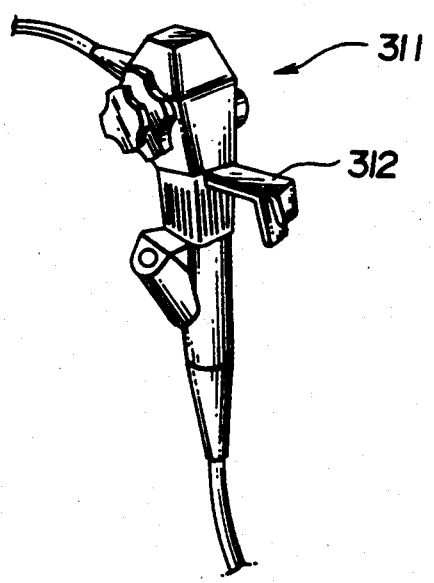
FIG. 2 is a perspective view of an endoscope holding and storing apparatus of the related art.
Figure 3:
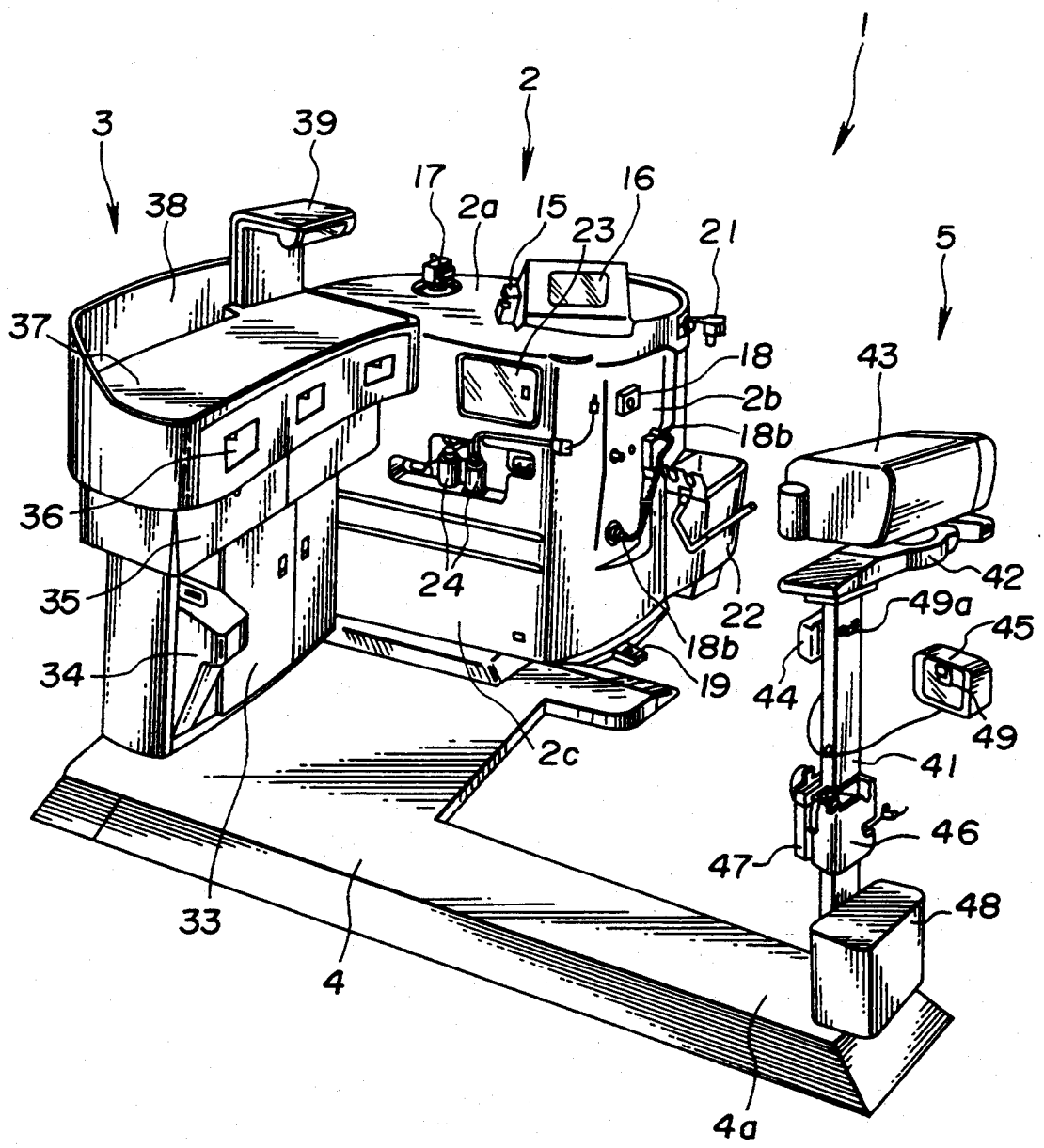
FIGS. 3 to 11 show the first embodiment.
Figure 4:
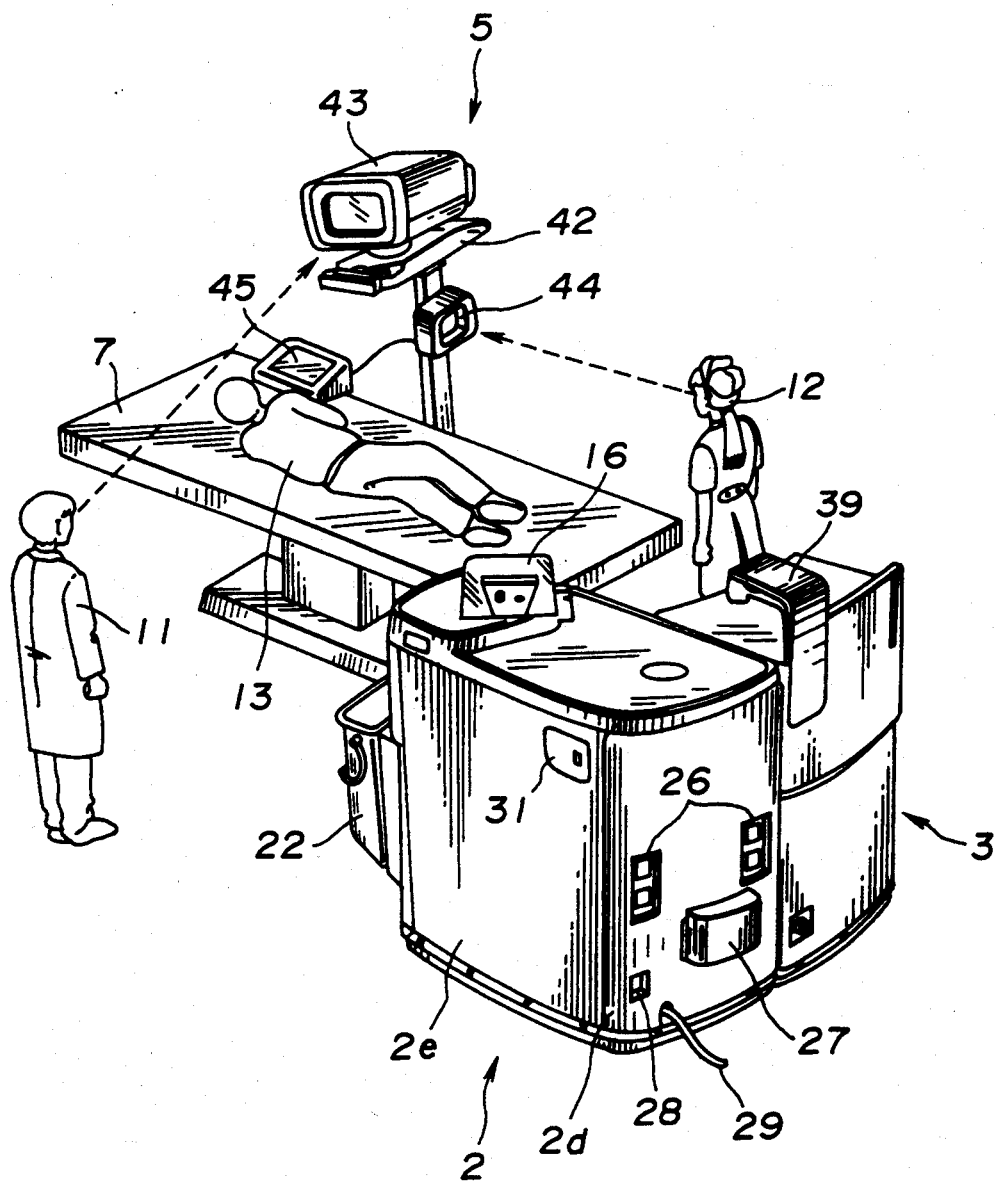

As shown in FIG. 3, an endoscope system 1 comprises an endoscope system storage rack (doctor work station) 2 on the inner left as an endoscope diagnosing apparatus, a nurse work station 3 on the left just before the endoscope system storage rack 2, a stand 4 forming an L-shaped plane from the bottom of the nurse work station 3 to the right thereof, and a monitor part 5 provided on a distal end part 4a in the right ahead direction of the stand 4. These parts 2, 3, 4, 4a and 5 form a main part of the endoscope system 1. A medical examination stand 7 is positioned on the system as shown in FIG. 4. For these arrangements, a doctor 11, a nurse 12 and a patient 13 are set as shown in FIG. 4.

As shown in FIG. 3, the endoscope system storage rack 2 is formed into an approximately rectangular parallelopiped having a gently curved side surface. On an upper surface 2a of the endoscope system storage rack 2, for example, an operation panel 16 to which a magnetic card reader 15 is attached, and a camera 17 are arranged. The magnetic card reader 15 is placed on the center facing sideways which can be used from both doctors and nurses even if water drips from the upper part so as to prevent water entering the inside of the endoscope system storage rack. A side surface facing forward 2b is provided with a connector 18 to which an endoscope is connected and the other connectors 18b, and can be fitted with an endoscope holder 21 and a storage case 22. A bed foot switch 19 is projecting from the lower part of the endoscope system storage rack 2. A lamp changing door 23 and a supplying water tank 24 are arranged on a side surface 2c facing the direction of the nurse work station 3 of the endoscope system storage rack 2.

As shown in FIG. 4, a duct 26, a cord cover 27, and a breaker 28 are arranged on a back side surface 2d of the endoscope system storage rack 2. A power source cord 29 is extended from the bottom of the back side surface 2d and connected to a power source (not illustrated). A maintenance door 31 is provided on the upper backward part of the side surface 2e of the opposite side of the nurse work station 3 of the endoscope system storage rack 2.

As shown in FIG. 3, a nurse work station door 33 on the lower part, a dust box 34 on the left side of the door 33, and a drawer 35 on the upper part of the door 33, and a tissue box door 36 on the upper part of the drawer 35. The upper surface of the nurse work station 3 is formed into a table-shaped plate 37. At the back of the upper surface, a back surface cover 38 like a single panel screen sticks out from the upper direction. On the right side of the back surface cover 38, a nurse work station light stand 39 is arranged.

The monitor part 5 is positioned on a pillar member 41 set on the distal end part 4a, and a plate-shaped monitor turn base 42 mounted on the distal end of the pillar member 41, and has a main monitor 43 which is mounted on the monitor turn base 42 and which can adjust a screen direction. Further, the monitor part 5 is provided with a nurse monitor 44 and a patient monitor 45 on the side surface of the upper part of the pillar member 41. A probe storage box 46, a P-plate storage box 47 and a hemadynamometer cover 48 are arranged on the lower side of the pillar member 41. The back surfaces of the nurse monitor 44 and patient monitor 45 are provided with a hook 49. The monitors 44 and 45 can be held by the hook 49 by hanging on a hook receiver 49a provided on the upper part of the pillar member 41.

Figure 5:
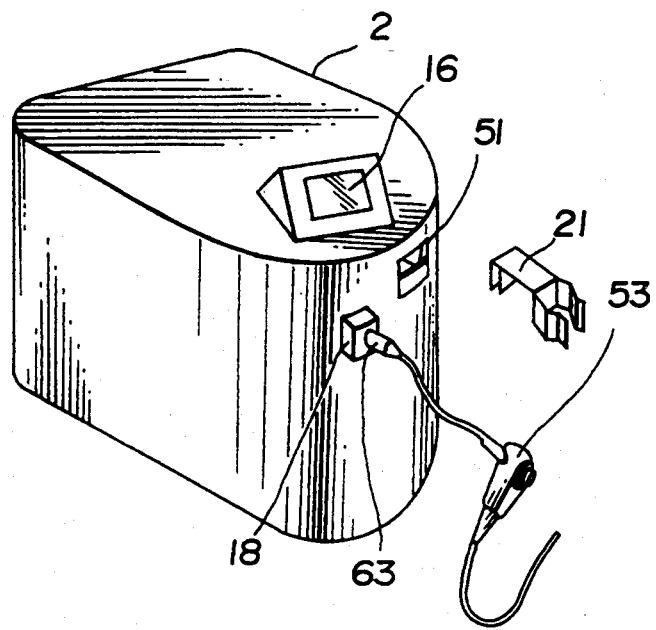

As shown in FIG. 5, a holding part 51, which is an engaged part, is formed on the right upper part of the front side surface of the endoscope system storage rack 2. An endoscope holder 21 is removably engaged with the holding part 51 and held. An endoscope 53 is connected to a connector 18 provided on the left lower side surface of the holding part 51 of the endoscope system storage rack 2.

Figure 6:
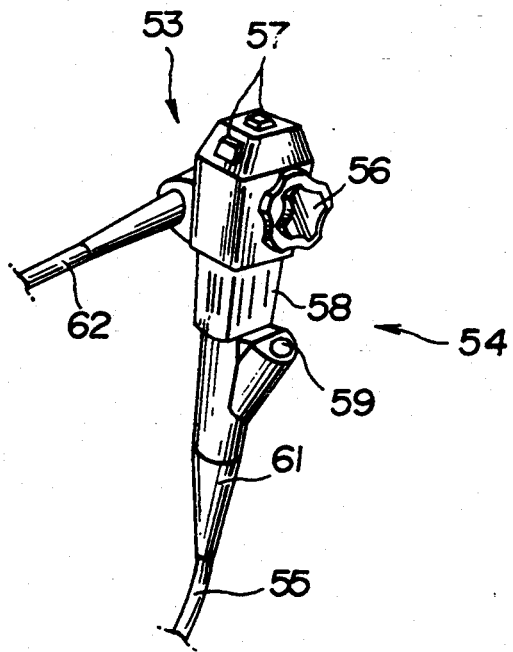

As shown in FIG. 6, in the endoscope 53, an elongated insertion tube 55 is extended from a proximal operation part 54. On the proximal end part, the proximal operation part 54 also has a curving operation lever 56 for curving a curved part (not illustrated) provided in the insertion tube 55, a switch 57, such as release for recording a video still image and freeze for stopping an image, and a gripping part 58. On the distal end part, the proximal operation part 54 also has a forceps channel aperture 59 and a circle taper part 61. An universal cord 62 is extended from the side surface of the operation part 54. A connector 63 (see FIG. 5) is provided at the distal end part of the universal cord 62. The endoscope 53 is connected to the connector 18 of the endoscope system storage rack 2 through the connector 63.

Figure 7:
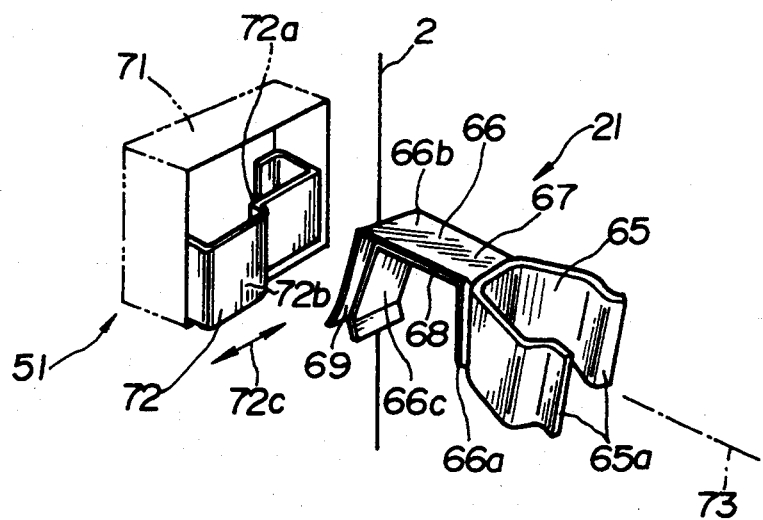

FIG. 7 is an enlarged perspective view of the endoscope holder 21 shown in FIG. 5.

An endoscope holding member 65 of an endoscope holder 21 is formed into a C-shape with an opening at one end using a plate-like member made of soft materials. Two distal end parts 65a of the C-shaped opening are bent outward with each other to make the engagement with the endoscope smooth. The endoscope holding member 65 is formed into a shape to be fitted to the shape of the gripping part 58 of the endoscope 53 shown in FIG. 6, for example, a shape having round apexes of a polygon. Since the endoscope holding member 65 is made of the aforesaid soft materials, it has flexibility so as to be able to open and close. The endoscope 53 is held by the endoscope holder 21 due to these opening and closing without dropping when engaged.

At the endoscope holder 21, an engaging member 66 of a downward U-shape is attached to the endoscope holding member 65 and formed of two plate-like members 67 and 68. A downward U-shaped distal end part 66a and an upper part of the distal end part 66b are stuck together to produce the engaging member 66. The two-plate like members 67 and 68 are formed to keep a space 69 between the two-plate like members 67 and 68 on a side of a base part 66c. The lower edge of the base part 66c of the engaging member is bent so that the aforesaid two plate-like members 67 and 68 face outward with each other.

The holding part 51 provided on the side of the endoscope system storage rack 2 is formed of a rectangular parallelopiped concave part 71 and a plate-like member 72 bent to be a shape engaged with the concave part 71. The plate-like member 72 has bending parts 72a bent in the lengthwise direction at the forward center part. The plate-like member 72 is provided with an U-shaped projected part 72b made of the bending part 72a. Thus, the base part 66c of the engaging member 66 of the endoscope holder 21 is inserted into the aforesaid two plate-like members 67 and 68 as if the endoscope holder 21 was sandwiched between the two plate-like members so as to be held. A width 72c of the U-shaped projected part 72b is formed to be fitted to the width of the engaging member 66 of the endoscope holder 21. The projected part 72b fixes the endoscope holder 21, so that, for example, the projected part 72b controls an axis 73 not to be rotated.

Figure 8:
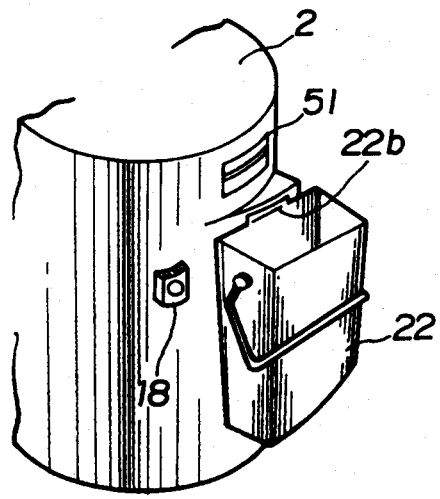

As shown in FIG. 8, a storage case 22 for transporting an endoscope is hung in a lower position of an engaged part 51 provided on the side surface of the endoscope system storage rack 2. When an endoscope is hung on the endoscope holder 21, the positions of the storage case 22 and endoscope holder 21 are determined in such way that the insertion tube of the endoscope enters the storage case 22.

Figure 9:
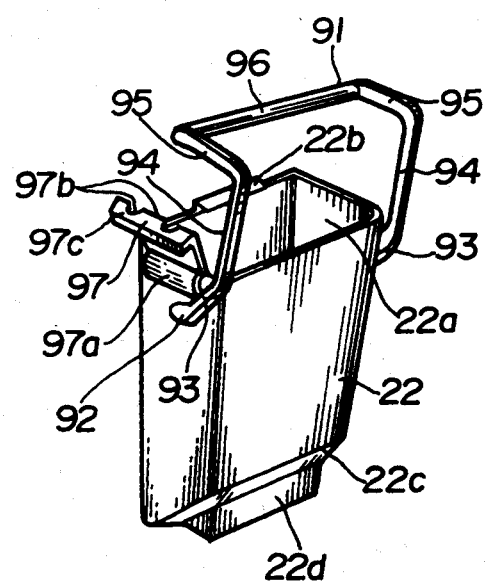

As shown in FIG. 9, when an endoscope is transported, the storage case 22 is used and shaped into an approximately oblong rectangular parallelopiped. The upper part of the storage case 22 opens and becomes an opening part 22a. A hook 22b is provided on the side of the opening part 22a facing the endoscope system storage rack 2. The storage case 22 is engaged with the endoscope system storage rack 2 using the hook 22b.

The storage case 22 is rotatably provided with a handle 91, which has a pair of inclined parts 93, straight parts 94 and handle side parts 95 at a rotation center 92. The storage case 22 is transported by gripping a rod member 96 having a section of a circle shape provided inside of the distal end part of the handle side parts 95.

When an endoscope is transported, a scope hook 97 for provisionally fixing the endoscope on the storage case 22 is removably attached on the left hand side surface of the opening part 22a of the storage case 22. The scope hook 97 has an attaching part 97a to be fitted to the opening part 22a. Above the fitting part 97a a scope setting part 97c having a concave part 97b fitted into the side shape of the endoscope is provided. The lower edge of the storage case 22 is an inclined surface 22c on which a convex part 22d like a triangle pole is formed.

Figure 10:
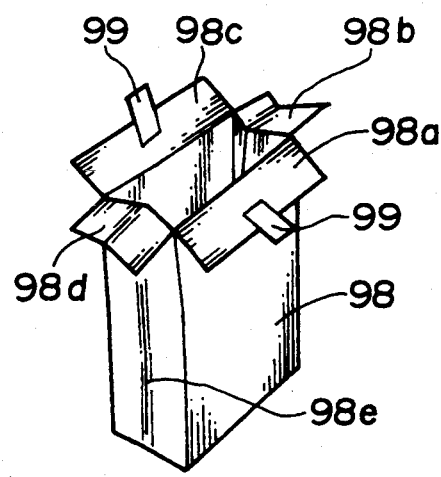

When an endoscope is transported, a disposable bag 98 as shown in FIG. 10 is attached to the inside of the storage case 22 to prevent the storage case 22 from being contaminated. The bag 98 is shaped into an oblong rectangular parallelopiped having an opening on the upper surface fitted into the shape of the storage case 22. The opening is provided with cover parts 98a, 98b, 98c and 98d. Tapes 99 are extended from these cover parts and stuck on the inside of the center of the cover parts 98a and 98b.

Figure 11:
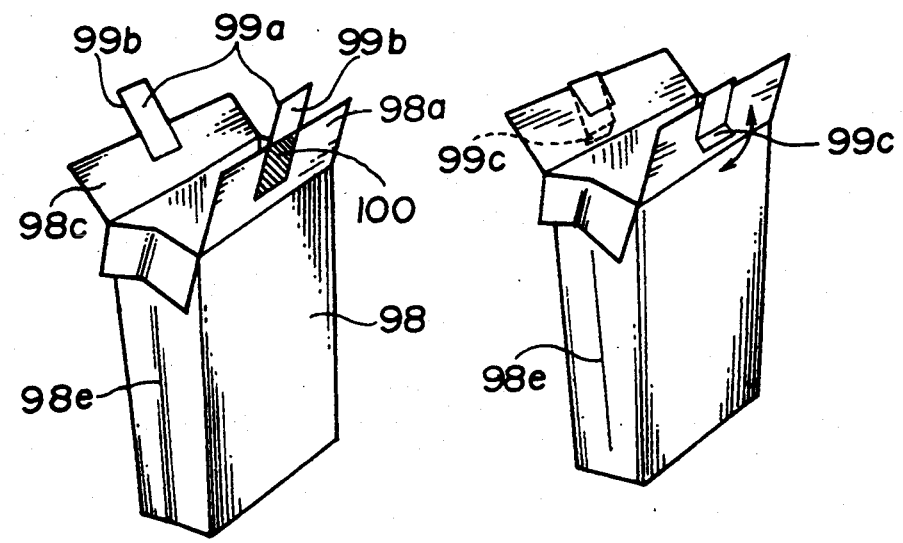

As shown in FIG. 11, the tapes 99 have a non-adhesive face 99a and adhesive face 99b. The distal ends of the tapes 99 are formed to be both non-adhesive faces 99c so as to easily carry the tapes. On the reverse sides of the places of the cover parts 98a and 98c on which the tapes 99 are stuck, peeling sheets 100 having the adhesive face 99b which can be stuck on or peeled from the disposable bag 98 several times is provided as shown in FIG. 11(b). The opening of the disposable bag 98 can be fitted to the opening part 22a of the storage case 22 so as to sufficiently open the bag in accordance with the shape of the opening part 22a using the tape 99 when the disposable bag 98 is attached to the storage case 22.

A crease 98e is made so that the disposable bag 98 can be folded up when it is not used.

Next, a using method of tile endoscope holder which is an endoscope holding apparatus will be explained.

The endoscope holder 21 is inserted into the U-shaped projected part 72b provided on the holding part 51 from the upper part to the lower part as if inserted into the space 69 between the two plate-like members 67 and 68 of the engaging member 66. Thus, the endoscope holder 21 is hung on the holding part 51 of the endoscope system storage rack 2 to be held. Then, a gripping part 58 of the endoscope 53 is inserted into a C-shaped opening of the endoscope holding member 65 of the endoscope holder 21 which is engaged with the endoscope system storage rack 2, so that the endoscope 53 can be held. When the endoscope 53 is used, the endoscope 53 is removed from the endoscope holding member 65 and used. In this way, the endoscope 53 can be attached to and removed from the endoscope holder 21 depending on the situation.

Next, in a case in which an operation ends and the endoscope 53 is washed, the endoscope holder 21 is removed from the holding part 51 and washed when the endoscope holder 21 holds a used endoscope. At the same time, in a case in which the storage case 22 directly stores a used endoscope instead of hanging the used endoscope on tile endoscope holder 21, the endoscope holder 21 stays clean and needs no washing.

An operator and an endoscope do not directly touch the holding part 51 provided on the side of the endoscope system storage rack 2 when they are used in the aforesaid manner.

As explained above, according to the first embodiment of the present invention, an endoscope which was used at an operation and unclean, and an endoscope holding apparatus which holds the endoscope are removed and washed after used. Therefore, it never occurs that another clean endoscope is contaminated with a contaminated endoscope holding apparatus because contaminated parts of an operator and endoscope touch the apparatus. Thus, spread of disease caused by germs obtained through the endoscope holding apparatus is prevented. Additionally, there is only a possibility that the endoscope holding apparatus is contaminated by touching a hand of the operator or the endoscope. Since the endoscope or a hand of the operator do not touch the engaged part with which the endoscope holding apparatus is engaged, a clean part and an unclean part can be differentiated and separated.

Figure 12:
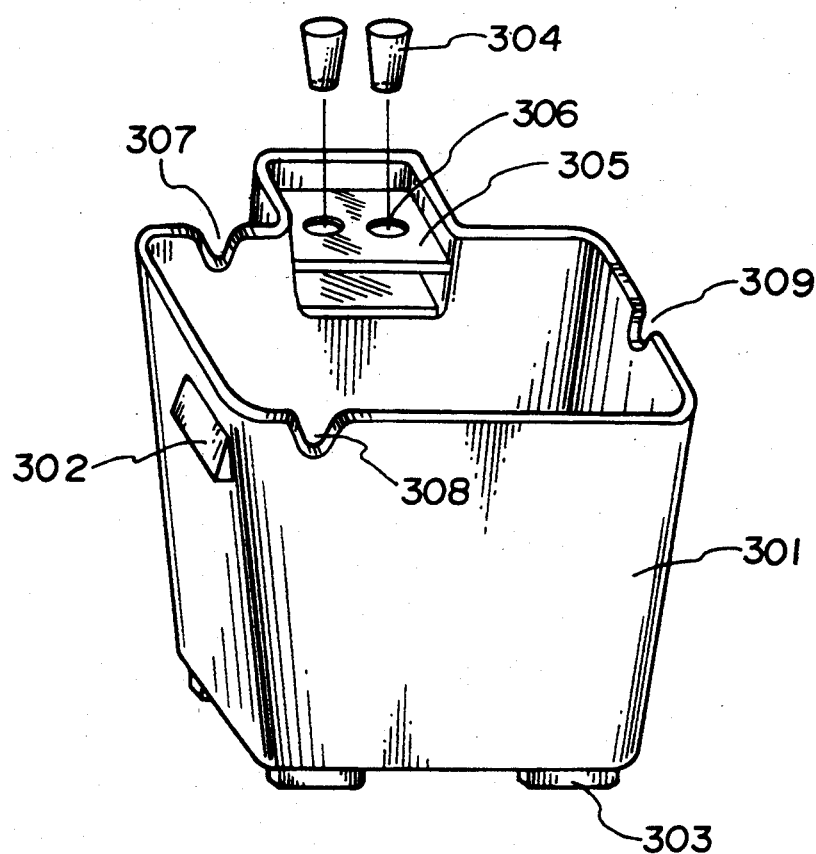
FIGS. 12 to 17 show other examples of storage cases.
Figure 13:
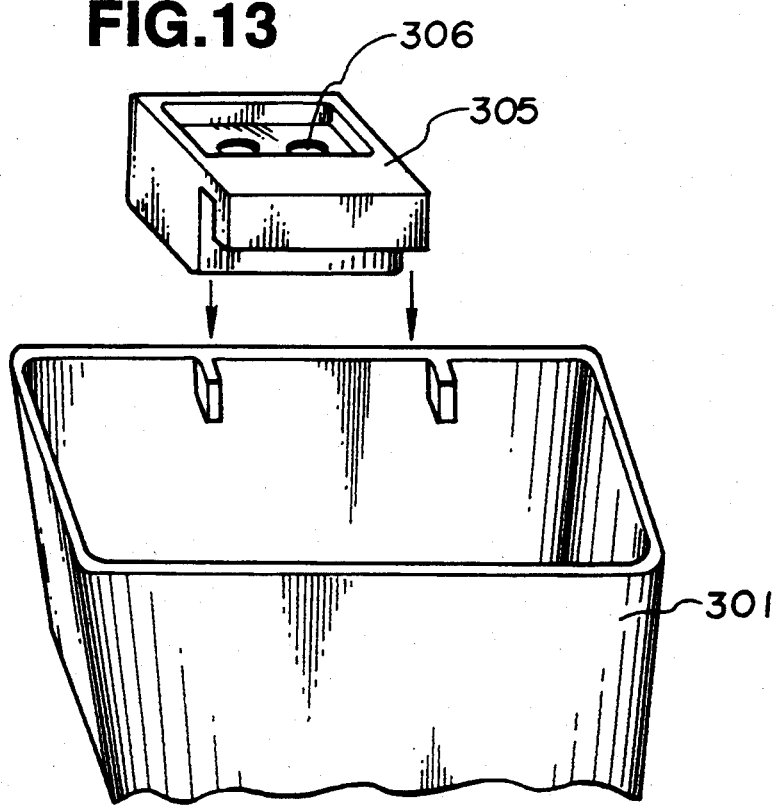

FIGS. 12 to 17 show other examples of the storage case 22 shown in FIG. 9. As shown in FIG. 12, a storage case 301 is formed into a shape having a wide opening and narrow bottom. On the external side of the storage case 301, a handle 302 for transporting the storage case 301 and a foot 303 for setting the case on the floor are provided. On the internal side of the storage case 301, a holding part 305 for holding a cup 304 which keeps liquid (water, alcohol, etc.) used for washing the endoscope are provided. As shown in FIG. 13, the cup holding part 305 may be separately formed from the main unit of the storage case 301 and removable from the storage case 301. Holes 306 are provided in the holding part 305 to hold the cup. The cup holding part may be a concave part fitted into a cup shape though it is not illustrated.

Figure 14:
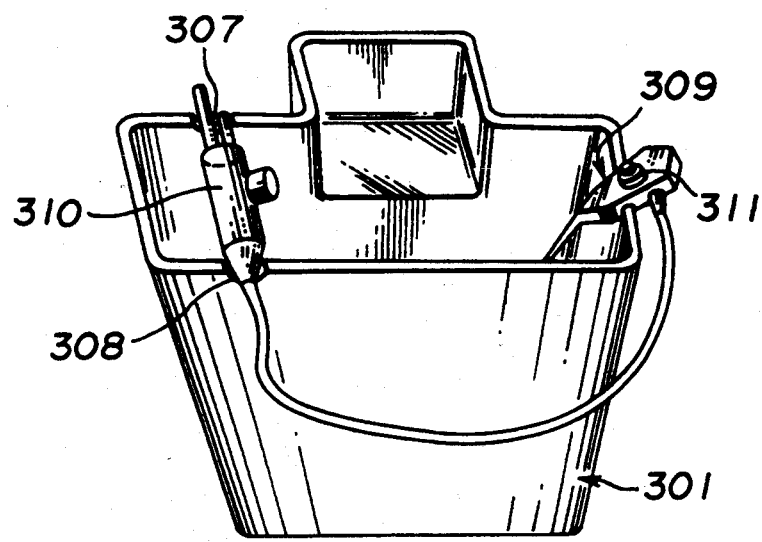

The storage case 301 has notch parts 307, 308 and 309 on the edge of the opening part to fix an endoscope which is stored in the case. As shown in FIG. 14, an endoscope can be held and fixed within the storage case using the notch parts 307, 308 and 309. In this state, the notch parts 307 and 308 hold an endoscope connecting connector 310 of an endoscope, and the notch part 309 holds an endoscope operation part 311. Because the notch parts 307 to 309 are used to hold the endoscope connecting connector 310 and the endoscope apparition part 311, the notch parts may be holes or concave parts fitted into respective shapes.

Figure 15:
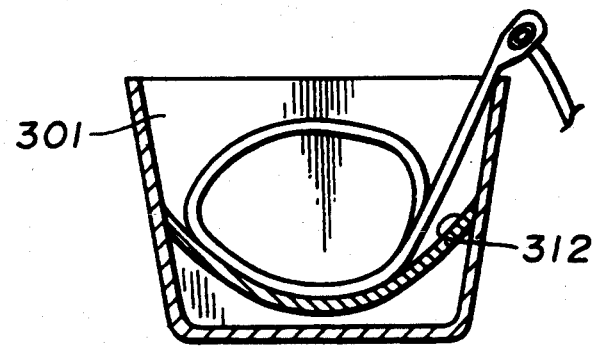

When the storage case 301 stores an endoscope, a bottom surface 312 is removably formed into a (concave) curved surface so as not to damage an endoscope insertion tube as shown in FIG. 15.

Figure 16:
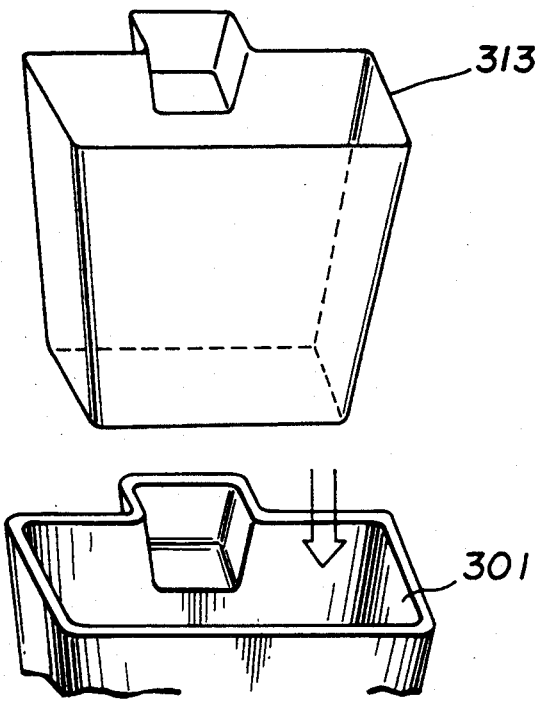
Figure 17:
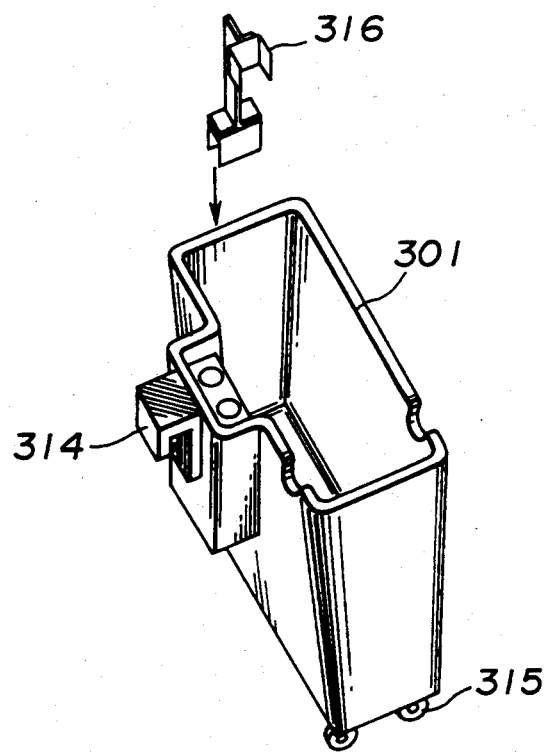

Here, a using method of the storage case 301 will be explained. As shown in FIG. 16, a disposable bag 313 made of plastic or paper is put in the inside of the storage case 301 at a washing area of an endoscope examination room, so that the bag covers the inside of the storage case. Next, an endoscope which has been already washed and disinfected is held in the storage case 301 as shown in FIG. 14 and also the cup 304 keeping water and alcohol is positioned in the case as shown in FIG. 12. After that, the storage case 301 is transported from the washing area to an examination bed or an examination area near an examination apparatus (endoscope system storage rack). The storage case 301 is fitted into the endoscope system storage rack, which is an examination apparatus, or a system cart using the hook 314 as shown in FIG. 17. Then, the connecting connector 310 of the endoscope is connected to the examination apparatus and the endoscope operation part is engaged with the endoscope holder of the endoscope system storage rack, so that the endoscope is hung and the endoscope insertion tube is kept within the storage case 301.

After a patient is examined using an endoscope, the endoscope is briefly washed and then put in the storage case 301 as shown in FIG. 14 to be transported to the washing area. At the washing area, the endoscope is taken out from the storage case to wash and disinfect the endoscope. The cup 304 is replaced with a new cup. In addition, the disposable bag 313 which is an inside bag of the storage case 301 is replaced with a new disposable bag 313 because it is contaminated by the used endoscope. In this way, that the disposable bag 313 is replaced with a new one in each examination prevents the storage case 301 from being contaminated, and therefore, prevents the endoscope from being contaminated.

In order to smoothly move the storage case 301 between both aforesaid areas, a caster 315 may be provided as shown in FIG. 17. Further, the endoscope holder 316 may be provided in the storage case 301 as a single unit, or as an independent unit and removable from the storage case 301. When the endoscope holder 316 is removable, for example, the endoscope holder attached to the endoscope system storage rack can be also used as the endoscope holder to be fitted to the endoscope system storage rack, and the endoscope holder may be attached to the storage case 301, and to the endoscope system storage rack, and then, to the storage case 301 while the endoscope holder is holding an endoscope.

Figure 18:
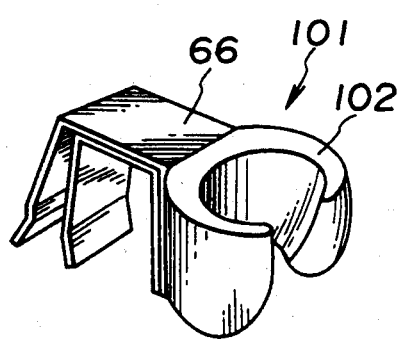
FIG. 18 is a perspective view showing a transformed example of an endoscope holder of a first embodiment of the present invention.

FIG. 18 is a transformed example of an endoscope holder related to the first embodiment.

An endoscope holding member 102 of an endoscope holder 101 is shaped into a C-shape using soft material with an opening at the distal end. The upper part side of the endoscope holding member 102 is formed into a wide diameter and the lower part side is formed into a taper of a small diameter. The shape of the endoscope holding member 102 is made to be fitted into a circle taper part 61 at the distal end part of the endoscope proximal operation part 54 of the endoscope shown in FIG. 5. The endoscope holder 101 of this transformed example is to hold the endoscope 53 using the circle taper part 61.

Figure 19:
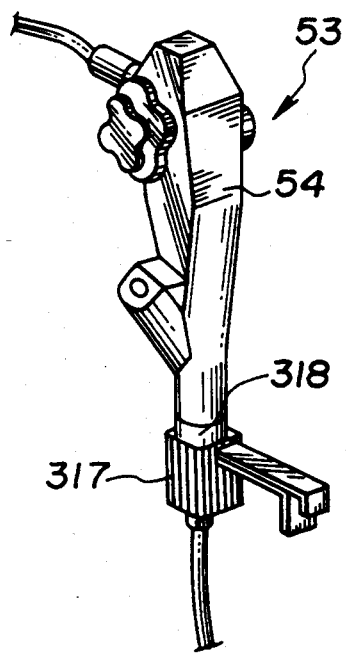
FIG. 19 is a perspective view showing another transformed example of an endoscope holder of the first embodiment of the present invention.

FIG. 19 is another example of an endoscope holder. An endoscope holder 317 holds a breaking protection part 318 (a taper part between an operation part and an insertion tube) of an endoscope.

Figure 20:
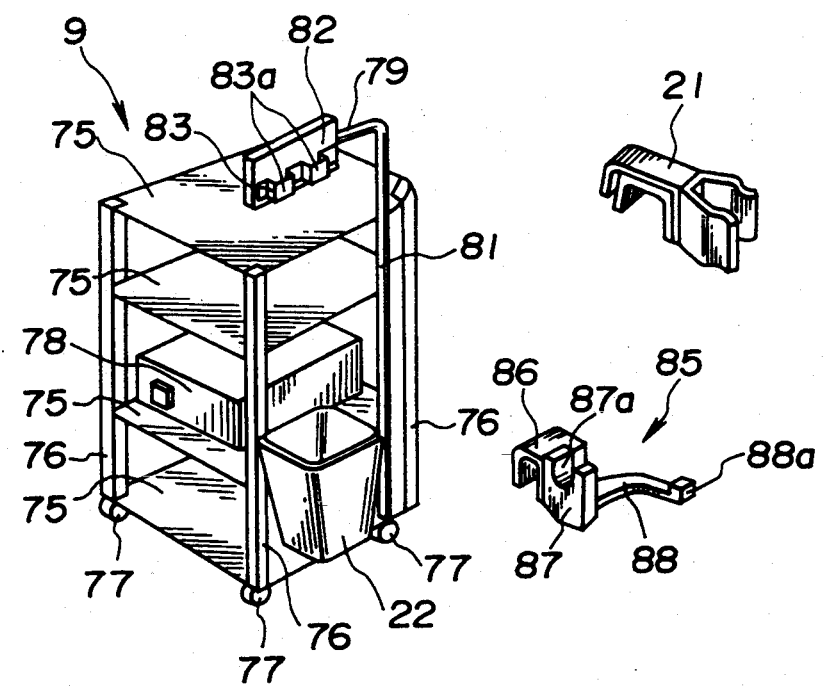
FIG. 20 is an explanatory diagram showing an example of a system cart of an endoscope holder and a storage case related to a second embodiment of the present invention.

FIG. 20 relates to the second embodiment of this invention and is a perspective view showing an example in which an endoscope holding apparatus is attached to a system cart.

An endoscope is not only used to be connected to the endoscope system storage rack explained in the first embodiment but also may be used to be connected to an endoscope apparatus mounted on a system cart shown in FIG. 20.

In a system cart 9, for example, four horizontal rectangular plate-like members 75 are arranged in the lengthwise direction and four corners of the members 75 are fixed with four pole members 76, and casters 77 are attached to the four corners of the bottom surface of the plate members. For example, an endoscope apparatus 78 is positioned on the system cart 9, which can freely move using the casters 77.

A scope hanger 79 is fixed on a side surface of the system cart 9. The scope hanger 79 has a pole member 81. The upper part of the pole member 81 is bent approximately vertically to set a plate-like holding part 82. For example, a thin plate member 83 having two convex parts 83a is fitted to the holding part 82 and an endoscope holders 21 and 85 having an engaging member for being fitted into and engaged with the convex parts 83a can be removably held. The endoscope holder 21 has the construction explained in the first embodiment. Further, a storage case 22 is arranged on the lower part of the convex part 83a to which the endoscope holder 21 is fitted.

The endoscope holder 85 has a plate-like member 86 which is an engaging member formed into a downward U-shape. An U-shaped member 87 which is provided approximately perpendicularly to the plate-like member 86 and on which a thick U-shaped concave part 87a is formed is provided to the side of the endoscope holder 85. An elongated extending member 88 having a slightly curved distal end part, and a small rectangular parallelopiped projection part 88a at the distal end of the elongated extending member 88 is provided on the endoscope holder 85.

An using method of the endoscope holder of the present embodiment is similar to that of the first embodiment. However, it is a different point that an endoscope is horizontally held when the endoscope holder 85 is used.

The second embodiment has the same operation and effects as those of the first embodiment.

Figure 21:
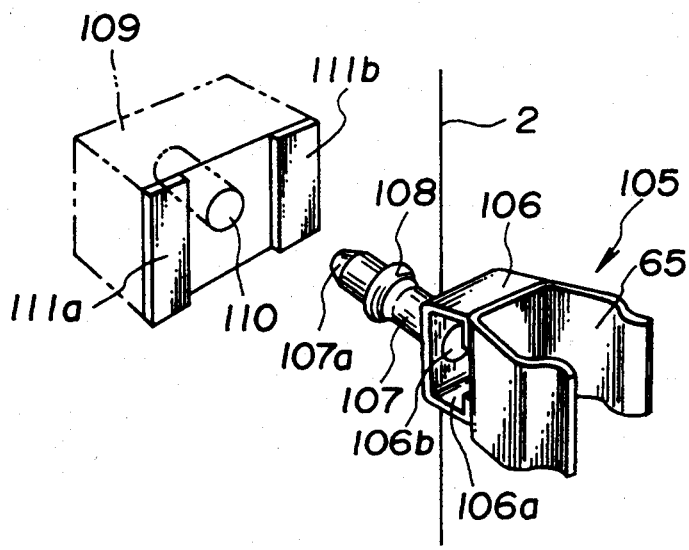
FIG. 21 is a perspective view showing an endoscope holder related to a third embodiment of the present invention and an attaching part provided on a side of an endoscope system storage rack.

FIG. 21 relates to the third embodiment of the present invention and is an enlarged perspective view of an endoscope holder and an engaged part provided on the side of an endoscope system storage rack.

An endoscope holder 105 has an endoscope holding member 65 at the distal end. The endoscope holding member 65 is similar to the endoscope holder 21 shown in the first embodiment. A C-shaped plate-like member 106 is formed into an approximate rectangle and fitted with a side of a C-shaped opening 106a. A connection hole 106b is provided on the opposite side of the side of the C-shaped opening 106a of the plate-like member 106 and a pin 107 is fitted into the hole 106b. A groove is produced on the distal end side of the pin 107. A C-ring 108 is inserted into the groove. The outer diameter of the C-ring 108 is made to be larger than the diameter of the pin 107. The distal end part 107a of the pin 107 is shaped into a taper.

At the same time, a block 109 is provided to the engaged part of the endoscope system storage rack. An engaging hole 110 which has the same size to which the pin 107 is fitted is bored on the center part of the front surface of the block 109. Oblong plate-like members 111a and 111b are attached on both sides of the opening part of the engaging hole 110. When the pin 107 is inserted into the engaging hole 110, a slid of the C-ring 108 is pressed. Because of the restitutive force of the pressed C-ring 108, the pin 107 has the structure in which the pin 107 does not come off easily. The plate-like members Ilia and 111b are provided to prevent the endoscope holder 105 from rotating around an axis which is the pin 107. That is, when the endoscope holder 105 is inserted into the engaging hole 110, the side surface of the plate-like member 106 is sandwiched and fixed between the two plate-like members 111a and 111b so as to control the rotation around the pin 107.

The third embodiment has the same operation and effects as those of the first embodiment.

Figure 22:
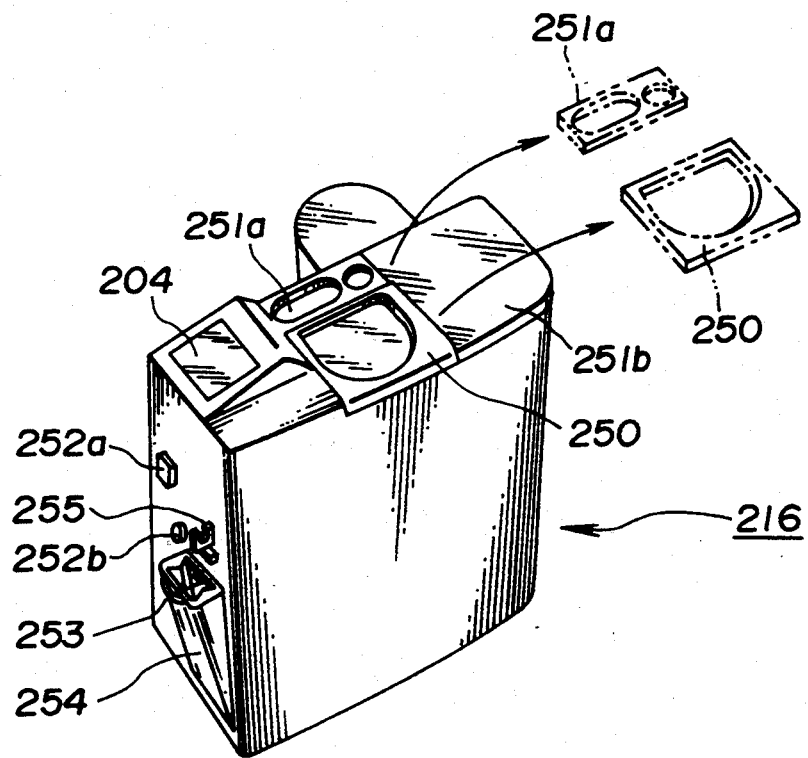
FIGS. 22 and 23 show another example of a storage case.

FIGS. 22 and 23 show an example of the appearance of the endoscope system storage rack 216 as an endoscope diagnosing apparatus. The endoscope system storage rack 216 accommodates an endoscopic light source and a video processor, which are described later. A centralized operation panel 204 for controlling on/off operations of the power supply for supplying power to each unit is formed in the upper front of the endoscope system storage rack 216. A removable endoscope tray 250 which loads a clean endoscope and removable accessory trays 251a and 251b which load treatment tools and other accessories necessary for endoscope examination are installed on the top of the endoscope system storage rack 216. Receptacles 252a and 252b for connecting an endoscope, an endoscopic light source, and a video processor, a storage case 254 which removably supports an endoscope holder 253 accommodating an unclean endoscope and which can be closed freely, and an endoscope holder 255 for holding an unclean endoscope are formed on the side of the endoscope system storage rack 216.

Figure 23A:
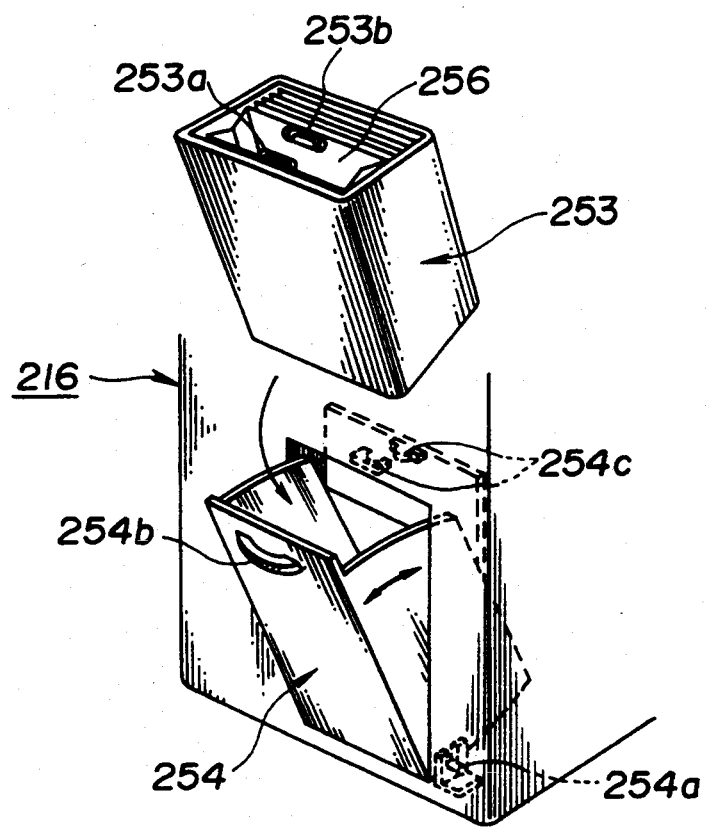
Figure 23B:
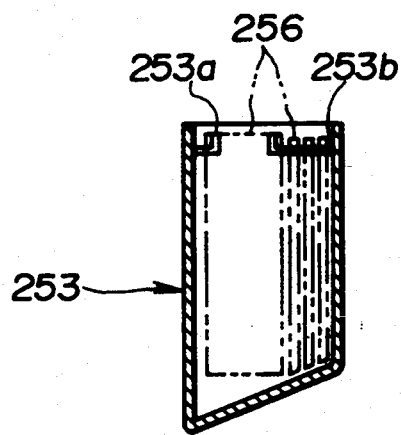

As shown in FIGS. 23(a) and 23(b), a rotatable axis 254a is installed at the bottom of the storage case 254. A hook 254b for drawing out the storage case 254 is projecting from the upper part of the storage case 254. A lock mechanism 254c is formed on the back end of the storage case 254 to lock the storage case 254 when the case is closed. The endoscope holder 253 has hooks 253a and 253b on its internal side. A plurality of disposable paper or plastic bags 256 are hung on the hooks 253a and 253b for storage. One of the disposable bags 256 is placed in the endoscope holder 253, and hung on the bag hooks 253a and 253b so that it will be open all the time to accept an endoscope. Other bags are stored behind the hook 253b to be used successively.

Figure 24:
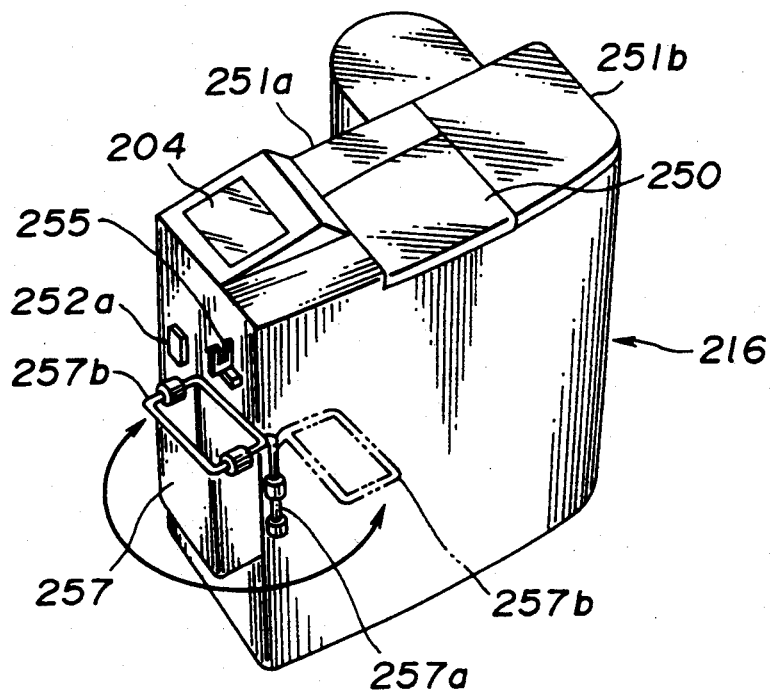
FIGS. 24 and 25 show another example of a storage case.
Figure 25:
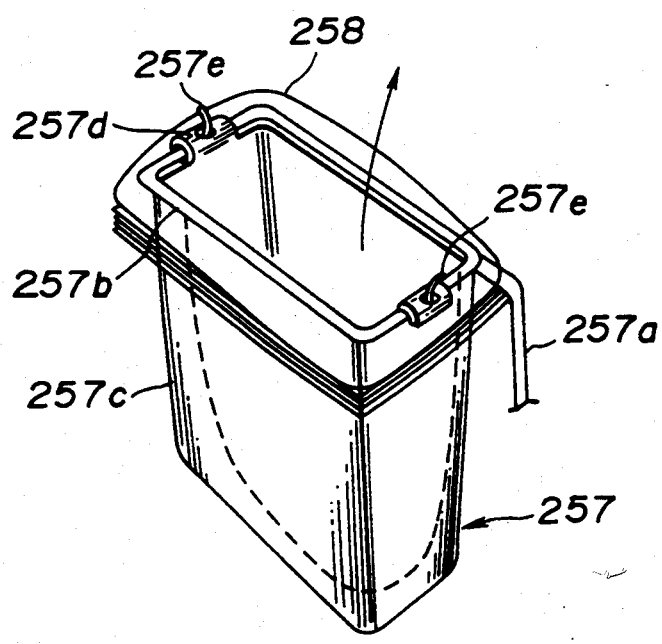

FIGS. 24 and 25 show other transformed example of a storage case differed from the storage case (bag) 254 shown in FIG. 23. A storage case 257 has a rotatable axis 257a on the side of an endoscope system storage rack 216. A mouth frame 257b is coupled to the axis 257a. A basket body 257c is provided so that it can be engaged with and removed from the frame 257b. The basket body 257c has locking hooks 257d on both sides of the opening part. The locking hooks 257d are hung on the frame 257b to hold the basket body 257c. Pins 257e are projecting from the holes of the locking hooks 257d, on which a plastic endoscope storage bag 258 placed in the main body 257c for storing an unclean endoscope is caught and fixed.

An unclean endoscope is stored in the endoscope storage bag 258 or a disposable bag 256. Thus, an user can carry the unclean endoscope to a washing room without making his/her hand dirty.

Figure 26:
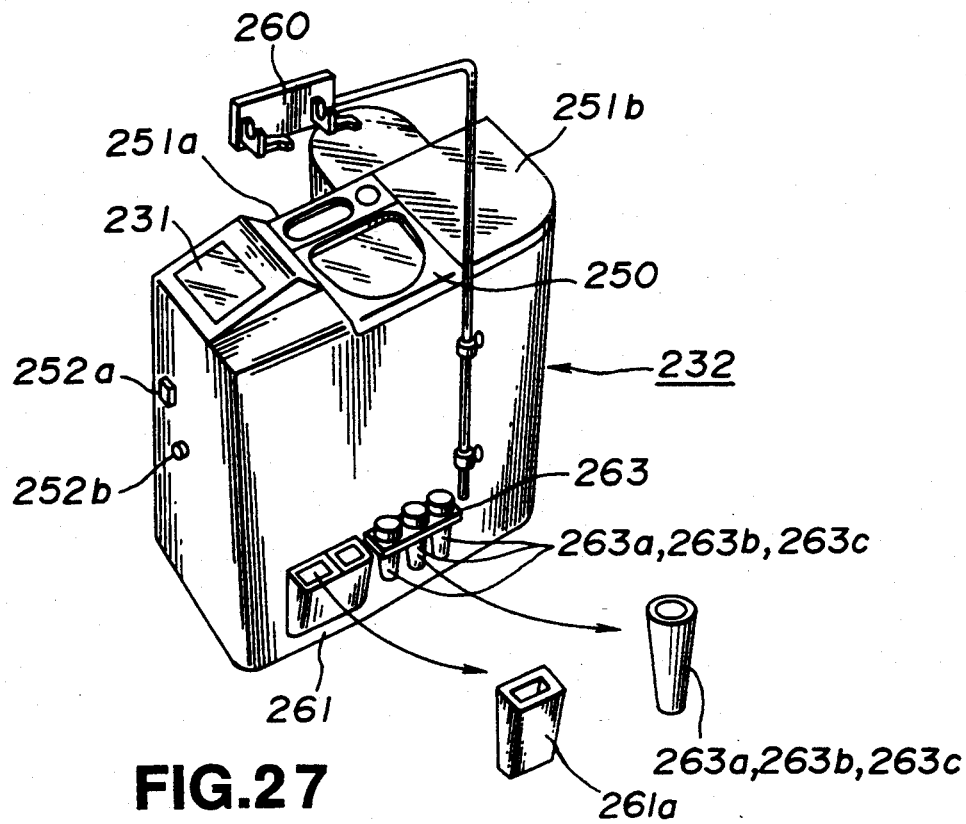
FIG. 26 is a perspective view of an endoscope system storage rack showing another example of an endoscope holder.

The centralized operation panel 231 is installed in the endoscope system storage rack 232 as shown in FIG. 26. An endoscope hanger 260 on which an unused or unclean endoscope is hung is formed on the side of the endoscope system storage rack 232. A storage bracket 261 for removably holding an endoscope end receptor 261a in which the distal end of an endoscope is mounted, and a bracket 263 for removably holding cups 263a, 263b, and 263c containing pure water or alcohol for washing an endoscope at hand on the lower side of the endoscope system storage rack 232.

Figure 27:
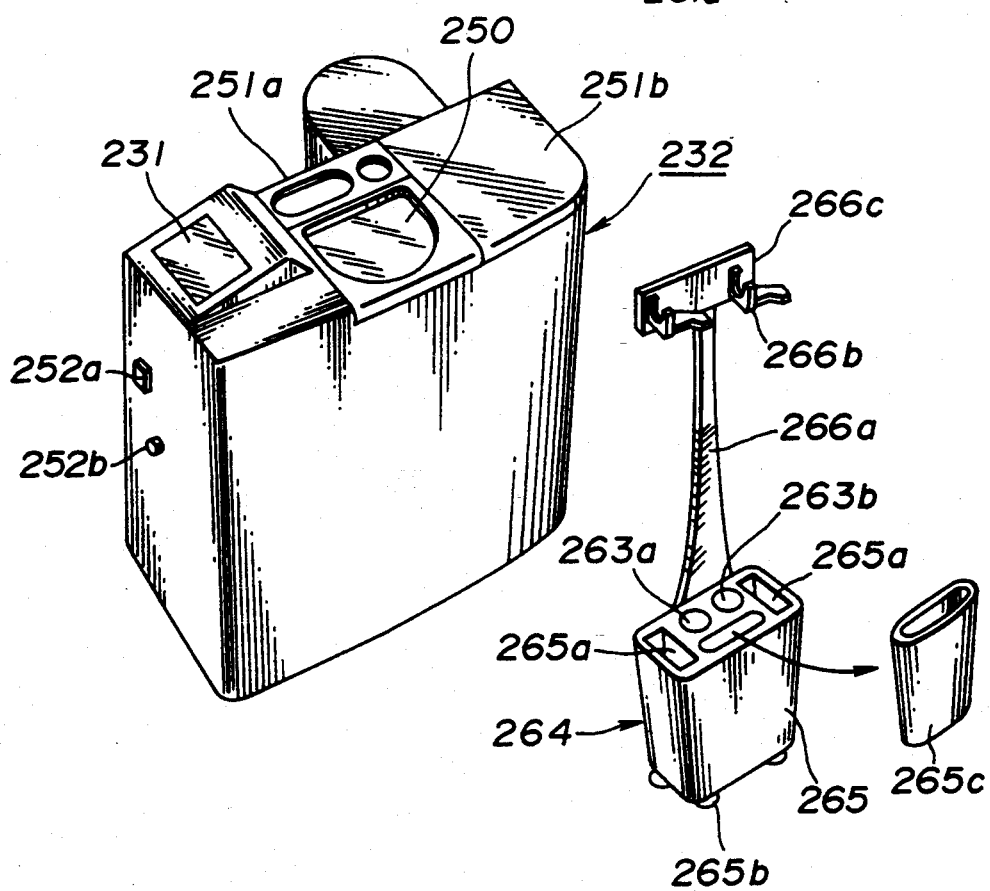
FIG. 27 is an explanatory diagram of an endoscope system storage rack showing another example of an endoscope holder.

FIG. 27 shows a mobile hanger trolley 264 which substitutes for the endoscope hanger 260 and is constructed as an independent unit. The hanger trolley 264 comprises a trolley main unit 265 in which a distal end receiving cup 265a for storing the distal end of an endoscope can be removably accommodated, a hanger section 266a extended from the top side of the trolley main unit 265, and a hook mounting plate 266c from which two hooks 266b are projecting and used to hang endoscopes on them. The trolley main unit 265 has four movable casters 265b on its bottom. In addition to the distal end receiving cup 265a, an empty cup 265c is also removably accommodated in the trolley main unit 265. Using the hanger trolley 264, unclean endoscopes can be held in the hanger trolley 264 and carried into a washing room, but not enclosed in bags.

Figure 28:
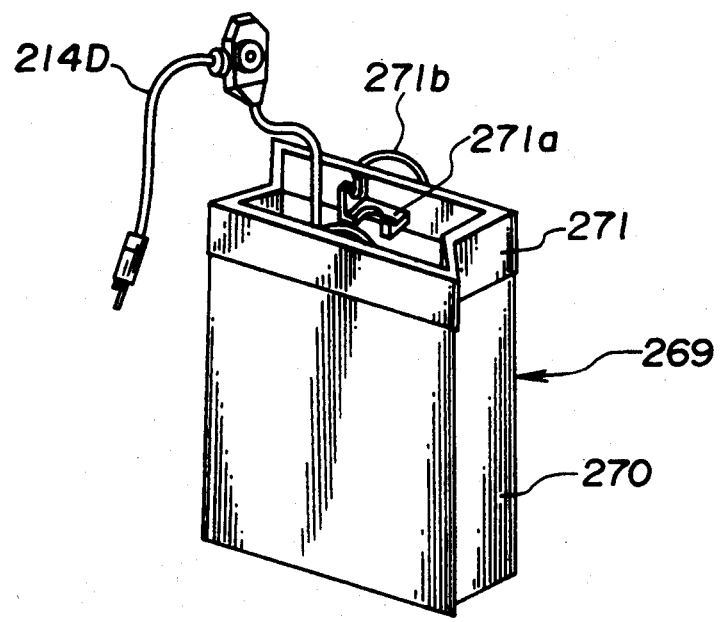
FIG. 28 is a perspective view showing another example of a storage case.

FIG. 28 shows a light-weight and compact endoscope disposable bag 269 comprises a bag 270 which is made from waterproof paper and used to store an unclean endoscope 214D, and a removable frame 271 made from elastic material to reinforce the opening part of the bag 270. The frame 271 includes a hook 271a for holding an endoscope inside the opening part and two grips 271b projecting above the opening part. Using the endoscope disposable bag 269, the unclean endoscope 214D can be put in the bag 270 perfectly. The grips 271b makes the endoscope disposable bag 269 portable.

Although it is not illustrated, the endoscope disposable bag 269 is used by combining with an endoscope holder provided on the endoscope system storage rack. When the endoscope is hung on the endoscope holder, the position on which the endoscope insertion tube is inserted into the disposable bag 269 is the same as that of the first embodiment.

Figure 29:
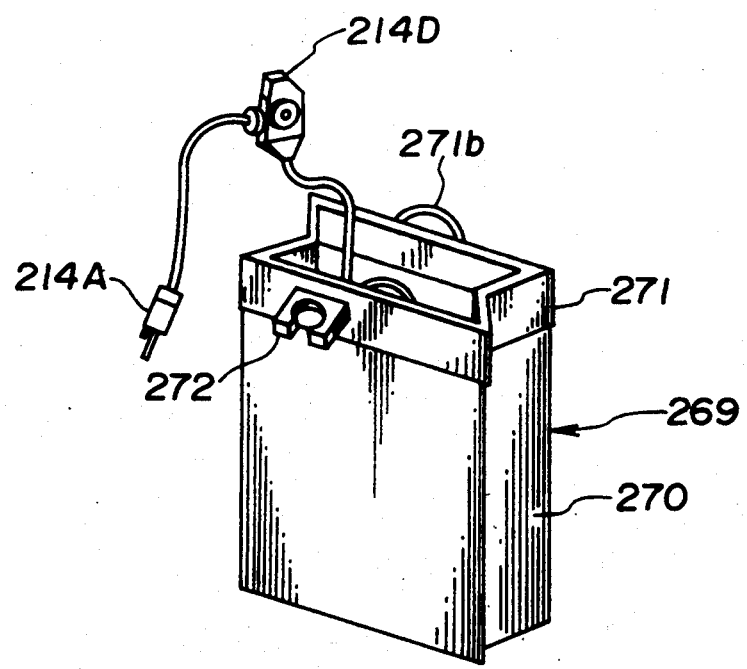
FIG. 29 is a perspective view showing another example of a storage case.
Figure 30:
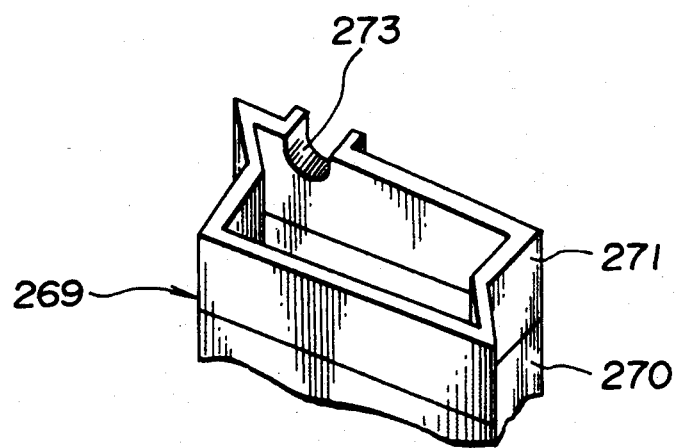
FIG. 30 is a perspective view showing another example of a storage case.
Figure 31A:
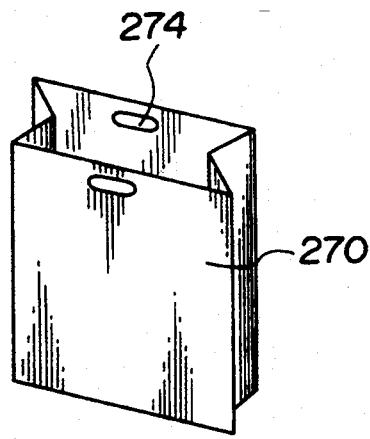
FIGS. 31(a) and 31(b) are explanatory diagrams showing another example of an endoscope holder and a storage case.
Figure 31B:
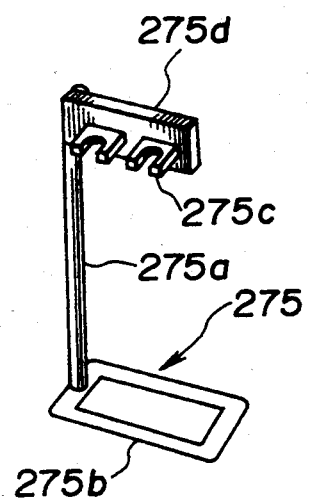

In FIG. 29, a hook 272 is provided on the external side of the frame 271 in the transformed example of the endoscope disposable bag 269 shown in FIG. 28. An unclean endoscope 214D can be carried with the distal end 214A locked in the hook 272. FIG. 30 shows an endoscope disposable bag 269 whose hook 273 is formed as part of the upper end of the frame 271. In the same way as the endoscope disposable bag 269 shown in FIG. 29, an unclean endoscope 214D can be carried with the distal end 214A locked. FIGS. 31(a) and 31(b) show an endoscope disposable bag in which a bag and a member for holding an endoscope are provided separately. A bag 270 shown in FIG. 31(a) is used to store an unclean endoscope and carried away. Holes 274 are formed as grips in the upper parts of the bag 270. An endoscope holder 275 shown in FIG. 31(b) comprises a stand 275b having an arm 275a provided vertically, and a hook mounting plate 275d having hooks 275c on which endoscopes are hung.

Figure 32:
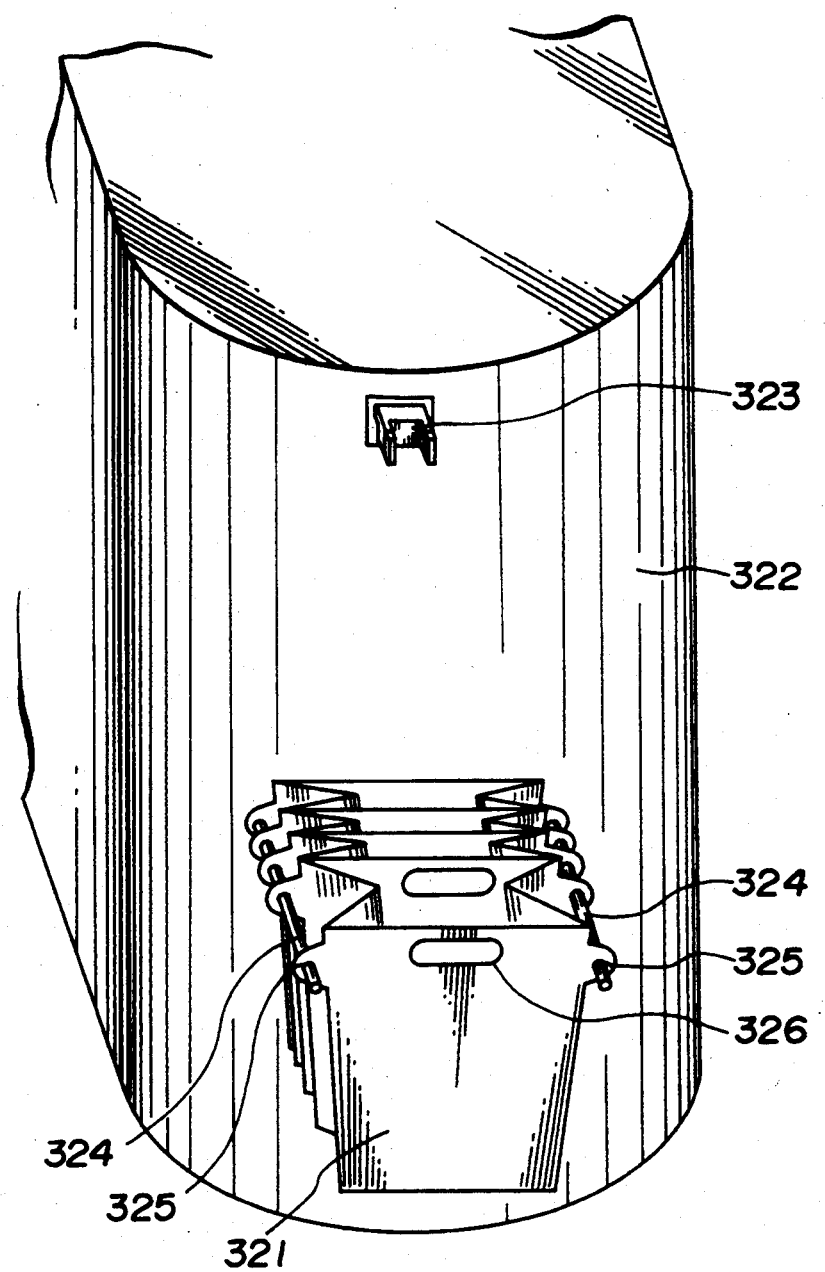
FIG. 32 is an explanatory diagram showing another example of a storage case.

FIG. 32 shows another embodiment of the storage case. Many endoscope bags 321 of this embodiment are folded, laminated, and arranged on the lower part of an endoscope holder 323 which is removably installed or fixed on an endoscope system storage rack 322. The endoscope bags 321 are disposable without having an outside case. The endoscope system storage rack 322 has a pair of bag holding stems 324 which is projecting in the horizontal direction. Insertion holding holes 325 provided on both sides of the lower part of the endoscope holder 323 are inserted into these stems 324 so that the endoscope bags are held. The endoscope bags 321 can be used from the bag 321 positioned on the external side. The endoscope bags 321 have holes 326 in their upper parts. Even in this embodiment, an endoscope which is hung on the endoscope holder 323 attached to the endoscope system storage rack 322 is inserted into the endoscope bags 321 (a bag positioned on the external side and its opening is opened) in which an insertion tube is placed on the lower position of the endoscope system storage rack while the endoscope is held.

In this invention, it is apparent that working modes different in a wide range can be formed on the basis of this invention without departing from the spirit and scope of the invention. This invention is not restricted by its specific working modes except as limited by the appended claims.

What is claimed is:

1. An endoscope holding and storing apparatus including an endoscope having an operational part and an insertion tube comprising:
   an endoscope system storage rack connected to said endoscope;
   holding means for holding at least a part of said endoscope; and
   a storage case located below said holding means for storing an insertion tube of said endoscope in a storable position when said endoscope is hung on said holding means,
   wherein said storage case includes a first attaching means for removably attaching said storage case to said storage rack, and
   wherein said storage rack includes a plate on one side of said storage rack and said holding means includes a gripping means for gripping said plate for removably attaching said holding means to said storage rack, wherein said gripping means is formed of two U-shaped plate-like members facing each other with a space between them.

2. The endoscope holding and storing apparatus according to claim 1, wherein said endoscope system storage rack is formed as a movable cart.

3. The endoscope holding and storing apparatus according to claim 1, wherein said holding means holds said operational part of said endoscope.

4. The endoscope holding and storing apparatus according to claim 1, wherein said holding means holds a breaking protection part provided in an insertion tube proximal end part of an endoscope.

5. The endoscope holding and storing apparatus according to claim 1, wherein said storage case includes a gripping part for gripping said endoscope.

6. The endoscope holding and storing apparatus according to claim 1, wherein said storage case is composed of waterproof bags constructed of a material which is easily folded.

7. The endoscope holding and storing apparatus according to claim 1, wherein said storage case includes an outer case and an inner case which is removable from the outer case.

8. The endoscope holding and storing apparatus according to claim 7, herein said inner case has an attaching part attachable to an opening of said outer case.

9. An endoscope holding and storing apparatus including an endoscope having an operational part and an insertion tube comprising:
   holding means detachably provided in an endoscope system storage rack which is connected to an endoscope, said holding means for holding at least a part of an endoscope, wherein said storage rack includes a plate on one side of said storage rack and said holding means includes a gripping means for gripping said plate for removably attaching said holding means to said storage rack, wherein said gripping means is formed of two U-shaped plate-like members facing each other with a space between them; and
   a storage case having a hook detachably connected to an opening in said storage rack and positioned below said holding means for storing at least said insertion tube of said endoscope when said endoscope is hung on said holding means.

10. The endoscope holding and storing apparatus according to claim 9, wherein said holding means is fixed to said examination system storage rack.

* * * * *